United States Patent [19]

Okazaki

[11] Patent Number: 5,258,539

[45] Date of Patent: Nov. 2, 1993

[54] PROCESS FOR RECOVERING A TRIALKYL PHOSPHATE ESTER FROM A TRIALKYL AND ARYL PHOSPHATE ESTER-BASED FUNCTIONAL FLUID

[75] Inventor: Mark E. Okazaki, Rodeo, Calif.

[73] Assignee: Chevron Research and Technology Company, San Francisco, Calif.

[21] Appl. No.: 968,654

[22] Filed: Oct. 30, 1992

[51] Int. Cl.⁵ ................................................. C07F 9/11
[52] U.S. Cl. ..................................... 558/150; 558/146
[58] Field of Search ................................ 558/146, 150

[56] References Cited

U.S. PATENT DOCUMENTS

| | | | |
|---|---|---|---|
| 4,438,048 | 3/1984 | Finley et al. | 260/982 |
| 4,443,384 | 4/1984 | Finley et al. | 260/982 |
| 4,482,506 | 11/1984 | Finley et al. | 260/982 |

FOREIGN PATENT DOCUMENTS 2704469 8/1978 Fed. Rep. of Germany .
1027059 4/1966 United Kingdom .

OTHER PUBLICATIONS

W. H. C. Rueggeberg et al.–The Journal of the American Chemical Society, 70, 1802 (1948).
H. D. Orloff et al.–The Journal of the American Chemical Society, 80, 727 (1958).
Morrison, R. T. and Boyd, R. N. *Organic Chemistry;* 4th Edition; Allyn and Bacon: Boston, (1983); pp. 549–550.

*Primary Examiner*—Mary C. Lee
*Assistant Examiner*—Michael Ambrose
*Attorney, Agent, or Firm*—W. K. Turner; J. J. DeYoung

[57] ABSTRACT

A process for recovering a trialkyl phosphate ester from a phosphate ester-based functional fluid by treating the fluid with an alkoxide salt, and thereafter, distilling the fluid to recover the trialkyl phosphate ester essentially free of aryl-containing phosphate esters and epoxide-containing hydrolysis inhibitors initially present in the fluid.

18 Claims, No Drawings

PROCESS FOR RECOVERING A TRIALKYL PHOSPHATE ESTER FROM A TRIALKYL AND ARYL PHOSPHATE ESTER-BASED FUNCTIONAL FLUID

BACKGROUND OF THE INVENTION

The present invention relates to a method of recycling phosphate ester-based functional fluids. More particularly, this invention is directed to a process for recovering a trialkyl phosphate ester from an trialkyl and aryl phosphate ester-based functional fluid such that the recovered trialkyl phosphate ester is essentially free of aryl-containing phosphate esters and epoxide-containing additives present in the functional fluid mixture.

Organic phosphate esters are commonly used as a synthetic base stock for various functional fluids. Due to their low flammability and low density, phosphate esters are particularly useful as a base stock for aviation hydraulic fluids. Presently, a majority of the commercial aircraft in operation around the world employ hydraulic fluids based on phosphate esters, and worldwide production of these fluids currently exceeds one million gallons annually.

These commercial aircraft generate a significant quantity of used aviation hydraulic fluid, however, and disposal of this used fluid is problematic. Most used aviation hydraulic fluid is currently either incinerated or buried in landfills. However, incineration is difficult, and therefore costly, due to the limited flammability of such fluids; and landfill burial is environmentally undesirable due to the potential for leakage of such fluids into groundwater. Accordingly, it would be particularly desirable to reduce the volume of used fluid that must be disposed of by recovering at least one of the major components of the used fluid for subsequent reformulation or other uses.

In this regard, used phosphate ester-based aviation hydraulic fluids typically contain a major amount of a phosphate ester base fluid and a minor amount of one or more functional fluid additives. The base fluid generally contains a trialkyl phosphate ester, such as tributyl phosphate, and lesser amounts of one or more aryl-containing phosphate esters. Therefore, to significantly reduce the amount of used fluid that must be disposed of, it would be particularly advantageous to recover a phosphate ester, such as a trialkyl phosphate ester, from such used fluids.

Liquid trialkyl phosphate esters, such as those used in aviation hydraulic fluids, can typically be purified by distillation. However, distilling used aviation hydraulic fluid to recover a trialkyl phosphate ester has heretofore been complicated by at least two factors.

First, as noted above, used aviation hydraulic fluids typically contain a trialkyl phosphate ester, such as tributyl phosphate, and one or more aryl-containing phosphate esters. The boiling points of the particular phosphate esters used in these fluids are often quite similar, and therefore, their separation by distillation is exceedingly difficult. For example, tributyl phosphate and dibutyl phenyl phosphate, two phosphate ester species commonly present in aviation hydraulic fluid, have boiling points of 183° C. and 200° C., respectively, at 22 mm Hg. Consequently, distilling used aviation hydraulic fluid to separate a trialkyl phosphate ester from the aryl-containing phosphate esters present in the fluid requires costly high efficiency distillation equipment and exacting procedures.

As a result, such separations are currently uneconomical when compared to disposal.

A second factor that complicates the recovery of a trialkyl phosphate ester from used aviation hydraulic fluid by distillation is the fact that some of the additives present in such fluids are sufficiently volatile to co-distill with the trialkyl phosphate. For example, epoxide-containing hydrolysis inhibitors, which are frequently present in phosphate ester-based hydraulic fluids to prevent or reduce hydrolysis of the phosphate esters, often co-distill with the trialkyl phosphate ester thereby contaminating the recovered fluid.

In view of the above, a need exists for an effective process which allows a trialkyl phosphate ester to be recovered from used aviation hydraulic fluid such that the reclaimed trialkyl phosphate ester composition is essentially free of the aryl-containing phosphate esters and epoxide-containing hydrolysis inhibitors initially present in the fluid. The present invention provides such a process, in part, by transesterifing the aryl-containing phosphate esters present in the fluid to form a trialkyl phosphate ester; and additionally by chemically modifying the epoxide-containing hydrolysis inhibitors present in the fluid to facilitate the subsequent separation of the trialkyl phosphate ester from such additives.

The transesterification of phosphate esters is known in the art. For example, W. H. C. Rueggeberg et al. in *The Journal of the American Chemical Society*, 70, 1802 (1948) describe the reaction of ethyl phosphate with n-butanol in the presence of sodium butylate to form diethyl n-butyl phosphate and ethyl di-n-butyl phosphate.

Similarly, H. D. Orloff et al. in *The Journal of the American Chemical Society*, 80, 727(1958) describe, among other reactions, the transesterification of dimethyl phenyl phosphate with sodium methoxide to form trimethyl phosphate and sodium phenoxide.

Additionally, British Patent Application No. 1,027,059, published Apr. 20, 1966, indicates on page 1, lines 23–26 that it is known that triarylphosphates can be transesterified with alcohols or polyols by heating in the presence of alkali metal hydroxides or alkali metal alcoholates.

Other methods of recycling used phosphate ester-based hydraulic fluids are also known in the art. German Patent Application No. 2,704,469, published Aug. 10, 1978, for example, discloses a process for the reclamation of used phosphate-ester hydraulic fluid contaminated with decomposition products, such as phosphoric acid and phenolates. The process includes mixing the fluid with water and separating the aqueous phase until the neutralization number of the fluid is less than 0.8; mixing the fluid with aqueous alkali and bleaching earth at an elevated temperature; and then separating the sludge phase, suspended fines and residual water from the hydraulic fluid.

SUMMARY OF THE INVENTION

The present invention provides a process for recovering a trialkyl phosphate from a phosphate ester-based fluid containing (i) a major amount of a base fluid comprising a trialkyl phosphate and one or more aryl-containing phosphate esters, and (ii) a minor amount of an epoxide.

The process comprises the steps of (a) contacting the functional fluid with a sufficient amount of an alkoxide salt to substantially transesterify the aryl-containing phosphate esters to form trialkyl phosphates and a phenol or a mixture of phenols and reaction of the epoxide to form alcohols; and thereafter (b) distilling the fluid mixture to obtain a distillate comprising at least about 90 weight percent trialkyl phosphate, the distillate being essentially free of the aryl-containing phosphate esters and the epoxide.

In a preferred embodiment of the present invention, the mixture of trialkyl phosphates, phenols and alcohols is contacted with an aqueous solution having a pH of about 10 or greater to substantially extract the phenol or mixture of phenols present therein; and then the remaining fluid mixture is distilled to separate the trialkyl phosphates is from the other components, particularly the alcohols formed from the epoxides.

Among other factors, the present invention is based on the surprising discovery that the aryl-containing phosphate esters present in a phosphate ester-based functional fluid can be readily transesterified with an alkoxide salt to form a trialkyl phosphate ester. Furthermore, the present invention is based, in part, on the unexpected finding that treating a used phosphate ester-based functional fluid with an alkoxide salt chemically modifies certain additives present in the fluid thereby facilitating the subsequent separation of the trialkyl phosphate ester from such additives.

DETAILED DESCRIPTION OF THE INVENTION

The process of the present invention is useful for recovering a trialkyl phosphate ester from a phosphate ester-based functional fluid, such as an aviation hydraulic fluid. The process is particularly suitable for a functional fluid containing (i) a major amount of a base fluid comprising a trialkyl phosphate and one or more aryl-containing phosphate esters, and (ii) a minor amount of an epoxide. The trialkyl phosphate ester composition recovered by the present process is essentially free of the aryl-containing phosphate esters and epoxide.

Typical phosphate ester-based functional fluids are described in U.S. Pat. No. 3,769,221, which is incorporated herein by reference. The present process is particularly useful for recovering tributyl phosphate from HyJet ® and Skydrol ® brand aviation hydraulic fluids and mixtures thereof. These hydraulic fluids are available from Chevron International Oil Company and Monsanto Chemical Company, respectively. Prior to describing the present process in greater detail, the components of a typical phosphate ester-based functional fluid will be further defined. A typical fluid contains a base fluid and various additives which are described below.

The Base Fluid

The base fluid of functional fluids finding use in the process of the present invention will contain a trialkyl phosphate and one or more aryl-containing phosphate esters. Typically, the base fluid will comprise at least about 70 weight percent, preferably about 75 to about 95 weight percent of the total functional fluid.

The particular species of phosphate esters present in the base fluid and the amount of each species present therein will vary depending on the source of the fluid. Typically, however, used phosphate ester-based functional fluid will contain predominately one trialkyl phosphate species and one or more aryl-containing phosphate ester species.

The total phosphate ester content of the base fluid will typically range from about 60 to about 100 weight percent, preferably from 75 to 100 weight percent, more preferably from 85 to 100 Weight percent of the base fluid.

The phosphate ester components of the base fluid have the general formula:

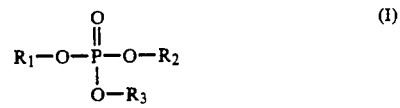

Wherein $R_1$, $R_2$, and $R_3$ each represent an alkyl group having 1 to about 12 carbon atoms, preferably 2 to 6 carbon atoms, more preferably 3 to 5 carbon atoms; or an aryl group having 6 to about 12 carbon atoms, preferably 6 to 9 carbon atoms.

As used herein, the term "trialkyl phosphate" refers to phosphate esters of Formula I above wherein $R_1$, $R_2$ and $R_3$ are each the same alkyl group; for example, tributyl phosphate. These trialkyl phosphates will typically contain 3 to about 36 carbon atoms, preferably 6 to 18 carbon atoms. The alkyl substituents of the trialkyl phosphate esters may be straight- or branched-chain alkyl groups and may be cyclic or acyclic. Typical alkyl groups include, for example, methyl, ethyl, n-propyl, isopropyl, n-butyl, iso-butyl, sec-butyl, n-pentyl, n-hexyl, cyclohexyl, n-heptyl, n-octyl, 2-ethylhexyl, iso-octyl and the like.

The term "mixed trialkyl phosphate" as used herein refers to a phosphate ester of Formula I above wherein $R_1$, $R_2$ and $R_3$ are each alkyl groups and at least one of the alkyl groups is different from the others; for example, dibutyl methyl phosphate or butyl ethyl methyl phosphate.

The term "aryl-containing phosphate ester" as used herein refers to a phosphate ester of Formula I above wherein at least one of $R_1$, $R_2$ or $R_3$ is an aryl group; and includes triaryl phosphates, such as triphenyl phosphate; alkyl diaryl phosphates, such as butyl diphenyl phosphate; and aryl dialkyl phosphates, such as dibutyl phenyl phosphate.

These aryl-containing phosphate esters will typically contain 8 to about 36 carbon atoms, preferably 18 to 27 carbon atoms. The aryl substituents of such phosphate esters may be phenyl or alkylphenyl groups, including both mono- and dialkyl-substituted phenyl groups, or mixtures thereof. The alkyl substituents of alkylphenyl groups will generally contain 1 to about 6 carbon atoms, preferably 1 to 3 carbon atoms; and include such alkyl groups as methyl, ethyl, n-propyl, isopropyl and the like. Exemplary alkylphenyl groups include tolyl, xylyl, isopropylphenyl (cumenyl) and the like.

As noted above, the base fluid will typically contain predominately one trialkyl phosphate species and one or more aryl-containing phosphate ester species. The trialkyl phosphate ester can be present in an amount ranging from about 10 to about 90, and more commonly 15 to 80 weight percent based on the total fluid with the remainder to make 100% Weight percent being an aryl-containing phosphate ester. Similarly, the aryl-containing phosphate ester or esters can be present in a total amount ranging from about 5 to about 95, and more commonly 10 to 85 weight percent based on the total fluid with the remainder to make 100 percent by weight being a trialkyl phosphate species.

Typical trialkyl phosphate esters which may be present in the base fluid and which may be recovered by the process of the present invention, include, for example, trimethyl phosphate, triethyl phosphate, tripropyl phosphate, tributyl phosphate, tripentyl phosphate, trihexyl phosphate, triheptyl phosphate and trioctyl phosphate and the like.

The present process is particularly suitable for functional fluids having a base fluid containing a trialkyl phosphate ester selected from the group consisting of tripropyl phosphate, tributyl phosphate, tripentyl phosphate and trihexyl phosphate. Most preferably, the base fluid will contain tributyl phosphate.

Typical aryl-containing phosphate esters which may be present in the base fluid, and which are transesterified by the present process to form the aforementioned trialkyl phosphates, include, for example, triphenyl phosphate, butyl diphenyl phosphate, dibutyl phenyl phosphate, diphenyl isopropylphenyl phosphate and the like. Preferably, the alkyl groups of any alkyl diaryl and aryl dialkyl phosphate ester species present in the base fluid will correspond to the alkyl group of the predominate trialkyl phosphate species in the base fluid.

Particularly preferred phosphate ester-based functional fluids for use in the present process will contain tributyl phosphate and one or more aryl-containing phosphate esters selected from the group consisting of butyl diphenyl phosphate, dibutyl phenyl phosphate, triphenyl phosphate, isopropylphenyl diphenyl phosphate, di(isopropylphenyl) phenyl phosphate, and tri(isopropylphenyl) phosphate and tertiary butylated trianyl phosphates such as diphenyl tertiary butyl phenyl phosphate.

In addition to the predominate trialkyl phosphate species, the base fluid may also contain minor amounts of other trialkyl phosphate species or mixed trialkyl phosphate species or mixtures thereof. Such minor phosphate ester species, in total, will generally be present in the base fluid in amounts of less than about 10 weight percent, preferably less than 5 weight percent based on the total fluid.

The base fluid may also contain, in addition to the phosphate esters described hereinabove, a variety of other base materials in minor amounts, such as organic amides of phosphorus acids; mineral oils; synthetic hydrocarbon oils; such as olefin oligomers, alkylated aromatics, polybutenes, and cycloaliphatics; organic esters, such as dibasic acid esters, polyol esters, and polyglycols; silicate esters; silicones; and halogenated hydrocarbons.

The Additives

Phosphate ester-based functional fluids will generally contain one or more functional fluid additives, such as an epoxide-containing hydrolysis inhibitor, a corrosion suppressant, an oxidation inhibitor, a viscosity index improver, a rust inhibitor, and a streaming potential inhibitor. Water may also be present in the fluid. These additives, in total, will generally comprise about 5 to about 25 weight percent of the functional fluid.

An epoxide-containing hydrolysis inhibitor is generally present in phosphate ester-based functional fluids to prevent or reduce hydrolysis of the phosphate ester base fluid. Typically, the epoxide-containing hydrolysis inhibitor will comprise about 0.1 to about 10 weight percent of the total fluid. A number of epoxide-containing Compounds are used for this purpose including, for example, glycidyl ethers, such as those described in U.S. Pat. No. 2,636,821.

A particularly useful class of epoxide-containing hydrolysis inhibitors, frequently present, for example, in aviation hydraulic fluids, are those derived from cycloalkyl compounds, such as alkyl-substituted 3,4-epoxycyclohexanes; monoepoxyendooxycyclohexyl compounds; monoepoxyethylenecyclohexyl compounds; 2-(3,4-epoxycycloalkyl-5,5'-spiro-3,4-epoxy) cycloalkyl-m-dioxanes, 3,4-epoxycycloalkyl-3,4-epoxycycloalkyl carboxylates, bis(3,4-epoxycyclohexyl) adipate and the like. These epoxides are further described in U.S. Pat. Nos. 3,637,507; 3,932,294; 3,969,254; 3,976,585; 3,983,046; 4,076,642; which are incorporated herein by reference.

As previously noted, epoxide-containing hydrolysis inhibitors are frequently difficult to separate from trialkyl phosphate esters by distillation, because the epoxide compounds often co-distill with the trialkyl phosphate. It has been discovered, however, that following treatment of a phosphate ester-based functional fluid containing such an epoxide with an alkoxide salt, the trialkyl phosphate ester component of the fluid can be recovered by distillation without significant contamination from the epoxide-containing hydrolysis inhibitor. This is believed to be due to the fact that the epoxide moiety of the hydrolysis inhibitor is ring-opened during the alkoxide treatment step to form higher boiling materials. By "higher boiling" it is meant at least 5° C. and preferably at least 10° C. difference in boiling point.

Oxidation inhibitors may also be present in the phosphate ester-based functional fluid. Typical antioxidants include hydroxy aromatics, such as 2,6-di(tert-butyl)-4-methylphenol and the like; and aromatic amines, such as diphenylamine, N-phenyl-α-naphthylamine and the like. Oxidation inhibitors generally comprise about 0.2 to 2.0 weight percent of the total fluid.

The functional fluid will also generally contain about 2 to 10 weight percent of one or more viscosity index improving agents, such as alkyl styrene polymers, polymerized organic silicones, polyisobutylene, or the polymerized alkyl esters of the acrylic acid series, particularly acrylic and methacrylic acid esters. These polymeric materials generally have a number average molecular weight of from about 2,000 to 300,000.

Rust control additives may also be present in the functional fluid in amounts ranging from about 0.2 to 2.0 weight percent. Examples of typical rust inhibitors include calcium sulfonates, such as calcium dinonylnaphthalene sulfonate; and calcium nonylbenzene sulfonate.

Additionally, phosphate ester-based aviation hydraulic fluids will generally contain a streaming potential inhibitor. Typical streaming potential inhibitors include, for example, perfluoroalkane sulfonic acids, such as trioctylammonium trifluoromethanesulfonic acid, potassium perfluorooctanesulfonate and the like; perfluoroalkane disulfonic acids; perhalometallic acids; and perhalometalloidic acids. Streaming potential inhibitors are generally present in aviation hydraulic fluids in an amount ranging from about 50 to about 1000 parts per million. These inhibitors are further described in U.S. Pat. Nos. 4,302,346; 4,206,067; 4,324,674; and 5,035,824; which are incorporated herein by reference.

Other specific additives may also be present in the functional fluid to impart particular properties, such as anti-wear and anti-foam agents.

The Process Conditions

In the process of the present invention, the used phosphate ester-based functional fluid is first contacted with an alkoxide salt to substantially transesterify the aryl-containing phosphate ester species present in the fluid thereby forming a trialkyl phosphate ester. Treatment of the fluid with the alkoxide salt is also believed to chemically modify certain additives present in the fluid, such as epoxide-containing hydrolysis inhibitors, thereby facilitating the subsequent separation of the trialkyl phosphate ester from such additives.

The alkoxide salt used to treat the fluid is generally selected such that the alkyl group of the alkoxide reagent corresponds to the alkyl groups of the predominate trialkyl phosphate ester present in the used fluid. For example, if the predominate trialkyl phosphate ester in the used fluid is tributyl phosphate, the used fluid will be contacted with a butoxide salt. Thus, the aryl-containing phosphate esters are substantially transesterified to form the trialkyl phosphate ester species that will subsequently be recovered.

The cation of the alkoxide salt may be any suitable organic or inorganic cation which does not interfere with the transesterification reaction. The salt must also have sufficient solubility in the reaction mixture so that the transesterification reaction may occur. Preferably, the cation is an alkali and alkaline earth metal cation, such as sodium, potassium, lithium, calcium, magnesium and the like. More preferably, the cation is sodium or potassium.

The alkali and alkaline earth metal alkoxides may be prepared by procedures which are well known in the art. For example, the preparation of sodium ethoxide is described in L. F. Fieser and M. Fieser, *Reagents for Organic Synthesis*, is Vol. 1, pp. 1065-1066, John Wiley and Sons, New York (1967) and references cited therein. Typically, these procedures involve reaction of an alcohol with an alkali or alkaline earth metal, such as sodium metal, or with an alkali or alkaline earth metal hydride, such as sodium hydride. In some cases, the alkali or alkaline earth metal alkoxide reagents are commercially available.

The used fluid is typically contacted with a sufficient amount of the alkoxide salt to substantially transesterify the aryl-containing phosphate esters present in the fluid. Generally, the fluid will be contacted with about 0.1 to about 5.0; preferably, 1 to 2 equivalents by molar weight of the alkoxide per molar equivalent aryl moieties contained in the phosphate ester based fluid.

The alkoxide reagent may be added neat to the functional fluid, or may be added as a solution or suspension in an inert organic solvent. Such inert organic solvents include aromatic hydrocarbons, such as benzene, toluene, xylene and the like. More preferably, the alkoxide salt will be prepared and added to the functional fluid as a 10 to 30 weight percent solution in the alcohol corresponding to the alkoxide; for example, sodium butoxide in butanol.

The alkoxide salt is typically contacted with the functional fluid at a temperature in the range of about 20 to about 200° C.; preferably, from 30° C. to 130° C. The reaction is typically conducted for a time sufficient to transesterify a majority, preferably greater than 95 percent, of the aryl-containing phosphate esters to form a trialkyl phosphate ester. Preferably, the reaction is conducted for about 0.1 hours to about 250 hours, more preferably, 1 hours to 24 is hours. Generally, the reaction is conducted at atmospheric pressure, however, the reaction can be conducted at higher or lower pressure, if desired.

In an Optional embodiment of the present invention, the used phosphate ester-based fluid may be pre-distilled prior to the transesterification step using procedures well-known in the art to separate the volatile components of the fluid from the substantially non-volatile components, such as a viscosity index improver, high-boiling aryl-containing s phosphate esters and the like.

Phenols are a by-product of the transesterification reaction. By the term "phenols", it is meant compounds having a hydroxyl group bonded directly to a benzene or benzenoid ring, including, but not limited to, the parent compound phenol ($C_6H_5OH$). Examples of phenols, include phenol, cresol, xylenol, isopropylphenol and the like. The particular phenolic compounds produced by the transesterification reaction and the amount of each phenol produced will, of course, be dependent on the particular aryl-containing phosphate ester species initially present in the functional fluid.

Upon completion of the transesterification reaction, the predominate trialkyl phosphate ester species present in the fluid is separated therefrom by distillation. The distillation can be conducted at atmospheric or reduced pressure, depending primarily on the boiling point of the trialkyl phosphate ester being recovered. For example, a distillation to recover tributyl phosphate will typically be conducted at a pressure in the range of about 1 to 50 mm Hg. One skilled in the art will be able to determine a suitable temperature and pressure for the distillation based on the literature-reported boiling point of the trialkyl phosphate ester being recovered.

In a preferred embodiment of the present invention, the alkoxide-treated functional fluid is contacted, prior to separation of the trialkyl phosphate ester, with an aqueous solution having a pH of about 10 or greater to substantially extract the phenols present in the fluid. Preferably, any alcohol corresponding to the alkoxide remaining in the fluid from the transesterification reaction will be substantially removed by stripping the treated fluid in vacuo prior to extraction with aqueous base.

The alkoxide-treated functional fluid will preferably be diluted with an inert solvent prior to extraction. Suitable inert solvents include aromatic hydrocarbons, such as benzene, toluene and the like, and aliphatic hydrocarbons, such as pentane, hexane and the like. Preferably, the inert solvent is hexane. The ratio of inert solvent to treated fluid will generally be in the range of about 0:1 to about 10:1, preferably about 0.5: 1.

The basic aqueous solution used for extraction may be prepared by dissolving, for example, the appropriate amount of sodium or potassium hydroxide in water to form a solution having a normality of about 0.5 to about 5.0, preferably 0.1 to 2, more preferably about 1.

To substantially extract the phenols, the functional fluid or a solution thereof is intimately contacted with the basic aqueous solution, and the organic layer then separated from the aqueous layer. Preferably, the functional fluid or a solution thereof is extracted at least twice, more preferably at least three times. Such extractions will generally remove at least about 50 weight percent, preferably at least 80 weight percent, of the phenols present in the fluid. After these extractions, the fluid is preferably washed with water to remove residual base and the trialkyl phosphate ester is then separated from the fluid by distillation.

The phosphate ester composition recovered by the present process will generally contain at least about 90 weight percent, preferably 95 weight percent, more preferably 98 weight percent, of a trialkyl phosphate ester. Generally, the recovered phosphate ester composition will be essentially free of aryl-containing phosphate esters and epoxide-containing hydrolysis inhibitors. By the term "essentially free of aryl-containing phosphate esters and epoxide-containing hydrolysis inhibitors", it is meant that the phosphate ester composition will contain less than about 2 weight percent, preferably less than 1 weight percent, more preferably less than 0.1 weight percent, of an aryl-containing phosphate ester or a mixture of such esters; and less than about 0.5 weight percent, preferably less than 0.2 weight percent, more preferably less than 0.1 weight percent, of an epoxide-containing hydrolysis inhibitor or a mixture of such inhibitors.

The advantages of the present invention will be readily apparent from consideration of the following examples. These examples are provided for the purposes of illustration and comparison only and should not be interpreted as limiting the scope of the present invention.

EXAMPLES

Analytical Method

Gas chromatography ("GC") was performed on a Hewlett-Packard HP 5880A instrument with a Supelco 10'×⅛" 5% OV-1 column with 80/100 Chromosorb WHP support. The GC program was as follows: Initial Value=150° C.; Initial Time=5.0 min.; Program Rate=10° C./min.; Final Value=300° C.; Final Time=10.0 min.; Post Value=150° C.; Post Time=2.0 min. and detection limit approximately 0.03 wt. %.

EXAMPLE 1

A 500 mL round-bottomed flask equipped with a magnetic stir bar and under nitrogen was charged with used aviation hydraulic fluid (200 g) containing 78.6 weight percent tributyl phosphate, 0.46 weight percent dibutyl phenyl phosphate, 0.15 weight percent butyl diphenyl phosphate, and 12.6 weight percent isopropylated triphenyl phosphates. To this sample was added a solution of sodium butoxide in butanol (20 weight percent, 132 g, 0.27 mol) over a period of 10 minutes. The resultant solution was allowed to stir at room temperature (23° C.) for 1 hour and then hexane (600 mL) was added and the organic layer washed with sodium hydroxide (1 N, 9×300 mL) and water (2×300 mL). The organic layer was dried over anhydrous sodium sulfate, concentrated in vacuo, and distilled (115°–120° C., 1 mm) to give 130 grams of a light yellow oil, which was found to contain 98.7 weight percent tributyl phosphate, 0 weight percent dibutyl phenyl phosphate, 0 weight percent isopropylated triphenyl phosphates and 0.68 weight percent phenols by GC analysis.

EXAMPLE 2

A sample of used aviation hydraulic fluid containing 56 weight percent tributyl phosphate, 23 weight percent dibutyl phenyl phosphate, 7 weight percent butyl diphenyl phosphate, and 4 weight percent isopropylated triarylphosphates was distilled (110°–125° C. at 2 mm Hg) to give a distilled fluid containing predominately tributyl phosphate (81 wt. %); dibutyl phenyl phosphate (15 wt. %); butyl diphenyl phosphate (1 wt. %); and epoxide (approximately 2 wt. %). This example demonstrates the difficulty in separating a used aviation hydraulic fluid into its various components by distillation alone.

EXAMPLE 3

To a 100 gram sample of this distilled fluid was added a solution of sodium butoxide (20 wt. %, 40 mL, 0.083 mol) in butanol over a period of 5 minutes. The reaction was allowed to stir at room temperature (about 23° C.) for 40 minutes and then aqueous sodium hydroxide (1N, 50 mL) and hexane (75 mL) were added. The organic layer was washed with aqueous sodium hydroxide (1N, 2×50 mL) and water (2×50 mL), and then distilled (115°–130° C. at 1 mm Hg) to give 83.6 grams of a light yellow liquid, which was found to contain 97.7 weight percent tributyl phosphate, less than 0.03 weight percent dibutyl phenyl phosphate, less than 0.03 weight percent butyl diphenyl phosphate, and less than 0.03 weight percent epoxide and 0.15 weight percent phenols by GC analysis.

What is claimed is:

1. A process for recovering a trialkyl phosphate from a fluid mixture said fluid mixture comprising (i) a major amount of a base fluid comprising a trialkyl phosphate and one or more aryl-containing phosphate esters, and (ii) a minor amount of an epoxide, said process comprising the steps of:
   (a) contacting said fluid mixture with an alkoxide salt whereby said aryl-containing phosphate esters are substantially converted to trialkyl phosphates and phenols and said epoxide is converted to an alcohol thereby forming a second fluid mixture containing trialkyl phosphates, phenols and alcohols; and
   (b) distilling said second fluid mixture to obtain a distillate comprising at least about 90 weight percent trialkyl phosphate, said distillate being essentially free of said aryl-containing phosphate esters and said epoxide.

2. The process according to claim 1 wherein said base fluid comprises at least about 70 weight percent of said fluid mixture and said epoxide comprises about 0.1 to about 10 weight percent of said fluid mixture.

3. The process according to claim 2 wherein said trialkyl phosphate contains 3 to about 36 carbon atoms and wherein said aryl-containing phosphate ester or esters contain 8 to about 36 carbon atoms.

4. The process according to claim 3 wherein said trialkyl phosphate is selected from the group consisting of tripropyl phosphate, tributyl phosphate, tripentyl phosphate, and trihexyl phosphate and wherein said aryl-containing phosphate ester or esters are each selected from the group consisting of butyl diphenyl phosphate, dibutyl phenyl phosphate, triphenyl phosphate, isopropylphenyl diphenyl phosphate, di(isopropylphenyl) phenyl phosphate, and tri(isopropylphenyl) phosphate.

5. The process according to claim 3 wherein said alkoxide salt is an alkali or alkaline earth metal salt and said fluid mixture is contacted with about 0.1 to about 5.0 equivalents by molar weight of said alkoxide salt per molar equivalent of aryl-containing phosphate esters in said fluid mixture.

6. The process according to claim 5 wherein said trialkyl phosphate is tributyl phosphate and said distillate contains less than about 1 weight percent of said aryl-containing phosphate ester or esters and less than about 0.2 weight percent of said epoxide.

7. A process for recovering a trialkyl phosphate from a fluid mixture said fluid mixture comprising (i) a major amount of a base fluid comprising a trialkyl phosphate and one or more aryl-containing phosphate esters, and (ii) a minor amount of an epoxide, said process comprising the steps of:
   (a) contacting said fluid mixture with an alkoxide salt whereby said aryl-containing phosphate esters are substantially converted to trialkyl phosphates and phenols and said epoxide is converted to an alcohol thereby forming a second fluid mixture containing trialkyl phosphates, phenols and alcohols; and
   (b) substantially removing said phenols from said second fluid mixture by contacting said second fluid mixture with an aqueous solution having a pH of about 10 or greater and separating a phenol-water extract phase from an organic phase containing trialkyl phosphates, and alcohols; and
   (c) distilling said organic phase to obtain a distillate comprising at least about 90 weight percent trialkyl phosphate, said distillate being essentially free of said aryl-containing phosphate esters and said epoxide.

8. The process according to claim 7 wherein said base fluid comprises about 75 to about 95 weight percent of said fluid mixture and wherein said epoxide comprises about 0.1 to about 10 weight percent of said fluid mixture.

9. The process according to claim 8 wherein said trialkyl phosphate contains 3 to about 36 carbon atoms.

10. The process according to claim 9 wherein said trialkyl phosphate is selected from the group consisting of tripropyl phosphate, tributyl phosphate, tripentyl phosphate, and trihexyl phosphate.

11. The process according to claim 10 wherein said trialkyl phosphate is tributyl phosphate.

12. The process according to claim 9 wherein said aryl-containing phosphate ester or esters contain 8 to about 36 carbon atoms 13. The process according to claim 12 wherein said aryl-containing phosphate ester or esters are each selected from the group consisting of butyl diphenyl phosphate, dibutyl phenyl phosphate triphenyl phosphate, isopropylphenyl diphenyl phosphate, di(isopropylphenyl) phenyl phosphate, and tri(isopropylphenyl) phosphate.

14. The process according to claim 12 wherein said epoxide is derived from a cycloalkyl compound.

15. The process according to claim 12 wherein said alkoxide salt is an alkali or alkaline earth metal salt and said fluid mixture is contacted with about 0.1 to about 5.0 equivalents by molar weight of said alkoxide salt per molar equivalent of aryl-containing phosphate esters in said fluid mixture.

16. The process according to claim 13 wherein said trialkyl phosphate is tributyl phosphate.

17. The process according to claim 7 wherein said distillate contains at least about 95 weight percent of said trialkyl phosphate.

18. The process according to claim 12 wherein said distillate contains at least about 98 weight percent of said trialkyl phosphate.

* * * * *

UNITED STATES PATENT AND TRADEMARK OFFICE
CERTIFICATE OF CORRECTION

PATENT NO. : 5,258,539

DATED : November 2, 1993

INVENTOR(S) : Mark E. Okazaki

It is certified that error appears in the above-identified patent and that said Letters Patent is hereby corrected as shown below:

Claim 13, Col. 12, line 13     "phenyl phosphate triphenyl" should read -- phenyl phosphate, triphenyl --

Signed and Sealed this

Twenty-third Day of August, 1994

Attest:

BRUCE LEHMAN

Attesting Officer     Commissioner of Patents and Trademarks